US011877918B2

(12) United States Patent
Blomström

(10) Patent No.: US 11,877,918 B2
(45) Date of Patent: Jan. 23, 2024

(54) PACKAGE OF ABSORBENT UNITS AND A METHOD FOR MANUFACTURING SUCH A PACKAGE

(71) Applicant: Essity Hygiene and Health Aktiebolag, Gothenburg (SE)

(72) Inventor: Philip Blomström, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 349 days.

(21) Appl. No.: 17/418,320

(22) PCT Filed: Feb. 15, 2019

(86) PCT No.: PCT/SE2019/050139
§ 371 (c)(1),
(2) Date: Jun. 25, 2021

(87) PCT Pub. No.: WO2020/167175
PCT Pub. Date: Aug. 20, 2020

(65) Prior Publication Data

US 2022/0062071 A1 Mar. 3, 2022

(51) Int. Cl.
*A61F 13/551* (2006.01)

(52) U.S. Cl.
CPC .............................. *A61F 13/55145* (2013.01)

(58) Field of Classification Search
CPC .......... A61F 13/55145; A61F 13/55135; A61F 13/5513; A61F 13/551; A61F 13/55105;
(Continued)

(56) References Cited

U.S. PATENT DOCUMENTS 8,220,632 B2 7/2012 Oi et al.
8,939,955 B2 1/2015 Oates
(Continued)

FOREIGN PATENT DOCUMENTS

AU 2010235860 A1 5/2011
CN 1592703 A 3/2005
(Continued)

OTHER PUBLICATIONS

Mokrzycki, W. S., et al., "Colour Difference" Machine Graphics & Vision, 2011, pp. 383-411, vol. 20, No. 4, The Library of The Swedish Patent and Registration Office. (Year: 2011).*
(Continued)

*Primary Examiner* — Javier A Pagan
(74) *Attorney, Agent, or Firm* — BUCHANAN INGERSOLL & ROONEY PC

(57) ABSTRACT

A package has an outer enclosure enclosing absorbent units and being at least partially non-opaque, wherein said outer enclosure has a thickness which is less than 70 μm, and wherein the outer enclosure is at least partly of a first predetermined colour and the absorbent units are at least partly of a second predetermined colour as viewed through the outer enclosure. The absorbent units have at least one lightly coloured or light grey area and the outer enclosure has a dominant area covering a substantial part of the area of the outer enclosure and having a lightness value above 75, and the colour difference between the dominant area and the lightly coloured or light grey area as seen through the outer enclosure is chosen so that the absorbent units are generally not visible through the outer enclosure.

19 Claims, 4 Drawing Sheets

1
2
3
4

(58) Field of Classification Search
CPC ...... A61F 15/00; A61F 15/001; A61F 15/003; B65D 85/00; B65D 85/62
See application file for complete search history.

(56) References Cited

U.S. PATENT DOCUMENTS

| | | | |
|---|---|---|---|
| 9,278,035 B2 | 3/2016 | Hashino et al. | |
| 9,308,139 B2 | 4/2016 | Hashino et al. | |
| 2007/0059453 A1 | 3/2007 | Benson | |
| 2007/0212502 A1 | 9/2007 | Hansborough | |
| 2007/0267322 A1 | 11/2007 | Kishida et al. | |
| 2008/0011642 A1 | 1/2008 | Oi et al. | |
| 2012/0310201 A1 | 12/2012 | Oates | |
| 2013/0098795 A1* | 4/2013 | Biber | A61F 13/55145 53/446 |
| 2013/0225730 A1 | 8/2013 | Allen et al. | |
| 2017/0151103 A1 | 6/2017 | Bianchi et al. | |
| 2022/0040012 A1 | 2/2022 | Blomström | |

FOREIGN PATENT DOCUMENTS

| | | |
|---|---|---|
| CN | 101442968 A | 5/2009 |
| CN | 101442969 A | 5/2009 |
| CN | 103140197 A | 6/2013 |
| CN | 103429204 A | 12/2013 |
| CN | 103889854 A | 6/2014 |
| CN | 206142077 U | 5/2017 |
| EP | 2623077 A1 | 8/2013 |
| EP | 2689757 A1 | 1/2014 |
| JP | 2000238875 A | 9/2000 |
| RU | 2505575 C2 | 1/2014 |
| RU | 2546482 C2 | 4/2015 |
| WO | 2007132434 A1 | 11/2007 |
| WO | 2012157620 A1 | 11/2012 |
| WO | 2020167175 A1 | 8/2020 |

OTHER PUBLICATIONS

Notification of the First Office Action dated Oct. 27, 2021, by the Chinese Patent Office in corresponding Chinese Patent Application No. 201980087896.2, and an English Translation of the Office Action. (17 pages).

Office Action dated Jan. 6, 2022, by the U.S. Patent and Trademark Office in U.S. Appl. No. 17/418,297.

Brainard, D.H., "Color Appearance and Color Difference Specification", The Science of Color, 2003, pp. 191-216, ISBN 0-444-512-519, Elsevier, Ltd. (26 pages).

International Preliminary Report on Patentability (PCT/IPEA/409) issued in corresponding International Patent Application No. PCT/SE2019/050138 dated Mar. 25, 2021. (10 pages).

International Search Report (PCT/ISA/210) and Written Opinion (PCT/ISA/237) dated Oct. 29, 2019, by the Swedish Patent Office as the International Searching Authority for International Application No. PCT/SE2019/050138. (12 pages).

International Search Report (PCT/ISA/210) and Written Opinion (PCT/ISA/237) dated Oct. 29, 2019, by the Swedish Patent Office as the International Searching Authority for International Application No. PCT/SE2019/050139. (15 pages).

Mokrzycki, W.S., et al., "Colour Difference ΔE—A Survey", Machine Graphics & Vision, 2011, pp. 383-411, vol. 20, No. 4, The Library of the The Swedish Patent and Registration Office (SLI04X00560E). (29 pages).

Written Opinion of the International Preliminary Examining Authority (PCT/IPEA/408) issued in corresponding International Patent Application No. PCT/SE2019/050138 dated Feb. 16, 2021. (5 pages).

Notification of the First Office Action issued in corresponding Chinese Patent Application No. 201980087889.2, dated Dec. 16, 2021; with English Translation. (16 pages).

Examination report issued in corresponding Australian Patent Application No. 2019429635, dated Nov. 23, 2021 (4 pages).

Third Party Observation issued in corresponding Mexican Patent Application No. MX/E/2021/091448, dated Dec. 14, 2021 (15 pages).

Opposition issued in corresponding Colombian Patent Application No. NC2021/0009298, the Opposition was filed on Oct. 26, 2021 and admitted on Nov. 22, 2021 (14 pages).

Office Action issued in corresponding U.S. Appl. No. 17/418,297, dated Feb. 7, 2022 (16 pages).

Office Action dated Dec. 21, 2021, issued in the corresponding Russian Patent Application No. 2021122389, 15 pages including 7 pages of English Translation.

Office Action dated Apr. 21, 2023, in corresponding Colombian Patent Application No. NC2021/0009298 and partial English translation. (13 pages).

Office Action (Examination Report No. 1) dated Mar. 24, 2022, by the Australian Patent Office in corresponding Australian Patent Application No. 2019429161. (2 pages).

Office Action (Notification of the Second Office Action) dated Apr. 11, 2022, by the Chinese Patent Office in corresponding Chinese Patent Application No. 201980087896.2, and an English Translation of the Office Action. (22 pages).

Office Action dated Mar. 31, 2022, by the Russian Patent Office in corresponding Russian Patent Application No. 2021126930, and an English Translation of the Office Action. (11 pages).

Applicant-Initiated Interview Summary dated May 17, 2022, by the U.S. Patent and Trademark Office in the U.S. Appl. No. 17/418,297.

Office Action (Decision of Rejection) dated Aug. 31, 2022, by the Chinese Patent Office in corresponding Chinese Patent Application No. 201980087889.2, and an English Translation of the Office Action. (10 pages).

Office Action (Notice of Acceptance) dated Aug. 29, 2022, 2022, by the Australian Patent Office in corresponding Australian Patent Application No. 2019429635. (3 pages).

The extended European Search Report dated Sep. 14, 2022, by the European Patent Office in corresponding European Application No. 19915477.4. (6 pages).

* cited by examiner

PACKAGE OF ABSORBENT UNITS AND A METHOD FOR MANUFACTURING SUCH A PACKAGE

TECHNICAL FIELD

The disclosure relates to a package of absorbent units. The disclosure also relates to a method for manufacturing a package of absorbent units.

BACKGROUND

Absorbent articles, for example in the form of sanitary napkins, panty liners, diapers and incontinence pads are well known. The general purpose of such absorbent articles is to absorb, distribute and store various types of body exudates while providing a high level of comfort and sense of dryness to the wearer during use. Also, such absorbent articles are arranged to prevent the wearer from getting the clothes soiled by body exudates.

For marketing and sale of absorbent articles, it is previously known to provide packages of such articles. Typically, a number of absorbent articles are formed as a stack which is contained within an outer enclosure, for example in the form of a flexible wrapping, so as to form a package. As a first alternative, each absorbent article can be enclosed in an individual wrapping material before such a stack is formed and enclosed within the outer enclosure. As a further alternative, the stack can be formed by a number of absorbent articles without any individual wrapping of each article.

According to prior art, the outer enclosure is normally produced from a relatively thin layer of a flexible material, such as polyethylene, which is formed as a bag-like outer enclosure. This means that a number of absorbent articles can be packed into the enclosure so as to form the final package of absorbent products.

During a packaging process, the outer enclosure is normally provided with various types of graphical items such as for example one or more logotypes and areas with printed text which indicate, for example, the name and type of product which is contained within the package. Furthermore, the basic material which is used for the outer enclosure is normally coloured or transparent when it enters the above-mentioned packaging process.

In order for the final package to give the customer a visual and aesthetic appearance which indicates that the absorbent product in question is a premium product which is of high quality, it has been proposed that the outer enclosure should be configured as a dark or opaque material so that any occurring graphical markings, logotypes or visual features on the actual absorbent products (or their individual wrapping material, if this is used) are not visible from the outside, i.e. so that they are not visible through the outer enclosure material. In other words, a "see-through" type of outer enclosure material is unwanted, in particular for the described premium products.

However, the design trends relating to today's absorbent consumer products may require that the outer enclosure is designed and manufactured in the form of very light or pale colours, i.e. colours having a relatively small amount of colouring substance. Also, the need for a cost-efficient manufacturing process may require that the outer enclosure is made from a very thin layer of material, suitably having a thickness which is not more than approximately 70 μm. This will result in an enclosure material which is at least partly non-opaque. Due to this, it has been noted that it is difficult to form the outer enclosure and the absorbent articles in a manner so as to avoid that graphical markings, logotypes, text areas or visual patterns on the absorbent products are actually visible from the outside, i.e. through the material of the outer enclosure. This is a disadvantage within the relevant field of technology.

In fact, even if the absorbent articles are not provided with any particular graphical markings such as logotypes or similar items, there may be a requirement that the absorbent articles or their wrapping material should not be distinctly visible from the outside. This means that, for a normal user, it must not be apparent that the absorbent articles inside the package are of any particular colour or form which, when regarded from outside the package, can be perceived as being substantially different from the colour of the outer enclosure. This applies in particular when the absorbent articles or wrapping material has an area which is at least partly coloured and the outer enclosure has an at least partly white or near-white area. In such a case, there is a tendency that the coloured section or area of the absorbent articles or wrapping material can be visible from the outside, i.e. as regarded through the outer enclosure.

It should be noted that the aesthetic qualities of the outer design of a package of absorbent articles is increasingly important due to the fact that it will affect the way in which the customers perceive the articles and their properties.

A previously known packaged absorbent product is described in the patent document US 2007/0267322. This document shows a package comprising a plurality of absorbent articles and at least one window. The package is based on a desire to show a graphic on at least one of the absorbent articles.

Even though the article disclosed in US 2007/0267322 discloses a package for a number of absorbent articles which is intended to give a customer a particular visual impression, there is a need for further improvements within this field of technology. In particular, there is an increasing requirement to provide an improved package which can be configured so as to indicate to a customer that the absorbent product in question has particular properties. In this regard, it is particularly important to give a user the impression that the products are of premium quality.

SUMMARY

In accordance with the disclosure, there is provided a package of absorbent articles having a purpose of solving the above-mentioned problems related to prior art within this field. In particular, there is provided a package which gives a particular visual impact to the customer and in particular in which no distinct difference in colour between the absorbent products and the outer enclosure can be is perceived by a viewer who watches the package from the outside of the outer enclosure of the package. In this regard, it should be noted that the absorbent products may or may not be provided with graphical items such as logotypes and similar items.

In accordance with the disclosure, this object is obtained by means of a package of absorbent units, said package comprising an outer enclosure enclosing said absorbent units and being at least partially non-opaque, wherein said outer enclosure has a thickness which is less than approximately 70 μm, and wherein the outer enclosure is at least partly of a first predetermined colour as defined in the L*a*b* colour space and the absorbent units are at least partly of a second predetermined colour in the L*a*b* colour space as viewed through the outer enclosure. Furthermore, the absorbent units have at least one lightly coloured or light grey area and the outer enclosure has a dominant area covering a substantial part of the area of the outer enclosure and having a lightness value above 75, and the magnitude of the colour difference between the dominant area and the lightly coloured or light grey area as seen through the outer enclosure is less than a predetermined limit value which is chosen so that the absorbent units are generally not visible through the outer enclosure.

According to the disclosure, an advantage is provided through the fact that it fulfills the object of giving the user of the absorbent article a positive visual impact regarding the properties of the article. In particular, generally no difference as regards the colour of the outer enclosure and the colour of the absorbent units can be perceived from the outside of the package.

A further advantage is provided in that the package will be more cost-effective to manufacture since the materials which can be used for the outer enclosure are relatively thin and also of relatively low opacity, which means that they are of relatively low cost.

Even though such materials are used, a visually appealing package is obtained.

The package may be configured so that the magnitude of the colour difference between the outer enclosure and the absorbent units as seen through the outer enclosure on no significant area exceeds 7.

The package may be configured so that the magnitude of the colour difference is less than 6, preferably less than 5, more preferably less than 4 and most preferably less than 3.

The package may be configured so that the outer enclosure has an opacity which is not higher than approximately 70%.

The package may be configured so that the opacity of the outer enclosure is less than 60%, preferably less than 50% and most preferably less than 40%.

The package may be configured so that the lightly coloured or light grey area has a lightness value which is at least 65, preferably in the range of 80-93, more preferably in the range of 85-93 and most preferably in the range of 89-93.

The package may be configured so that the dominant area constitutes at least 50% of the total area of the outer enclosure, preferably at least 60%, more preferably at least 70% and most preferably at least 80% of said total area.

The package may be configured so that the dominant area has a lightness value which is above 80, preferably above 85 and most preferably above 90.

The package may be configured so that the first predetermined colour has a first colour value which is within the interval from −22 to +26 and a second colour value which is within the interval from −25 to +23.

The package may be configured so that the thickness is less than approximately 60 μm and most preferably less than 50 μm.

The package may be configured so that the outer enclosure supports a first graphical item and at least one of said absorbent units supports a second graphical item, and wherein the absorbent unit is configured so that said second graphical item is positioned in a manner in relation to said first graphical item so that said second graphical item is not visible through the outer enclosure.

The package may be configured so that each one of said absorbent units is constituted by an inner enclosure which encloses an absorbent product, and wherein said second graphical item is positioned on the outside of said inner enclosure.

The package may be configured so that each one of said absorbent units is constituted by an absorbent product, and wherein said second graphical item is positioned on said absorbent product.

The package may be configured so that said second graphical item is positioned so that it faces the inside of the outer enclosure and wherein said first graphical item covers said second graphical item.

The package may be configured so that the absorbent unit supporting said second graphical item is configured so that the second graphical item faces inwards into said outer enclosure.

The package may be configured so that said first graphical item is arranged on the exterior side of said outer enclosure.

The package may be configured so that said first graphical item and said second graphical item are constituted by printed areas or areas comprising coloured sections, adhesive stickers, logotypes, text boxes or graphical markings.

The package may be configured so that said absorbent unit is arranged in a folded configuration.

According to the disclosure, there is also provided a method for manufacturing a package of absorbent units, said method comprising: providing an outer enclosure which is at least partially non-opaque and which has a thickness which is not more than approximately 70 μm; arranging said outer enclosure so that it encloses said absorbent units; providing the outer enclosure at least partly with a first predetermined colour as defined in the L*a*b* colour space; and providing the absorbent units at least partly with a second predetermined colour in the L*a*b* colour space as viewed through the outer enclosure. Furthermore, the method comprises: providing the absorbent units with at least one lightly coloured or light grey area; providing the outer enclosure with a dominant area covering a substantial part of the area of the outer enclosure and having a lightness value above 75, and configuring the package so that the magnitude of the colour difference between the dominant area and the lightly coloured or light grey area as seen through the outer enclosure is less than a predetermined limit value which is chosen so that the absorbent units are generally not visible through the outer enclosure.

Further advantages and advantageous features of the disclosure are disclosed in the following description and in the dependent claims.

In the following, the term "absorbent unit" is used to indicate either a unit in the form of an absorbent article including an individual wrapping or a unit in the form of an absorbent article without such individual wrapping. The disclosure is consequently equally applicable to packages comprising either one of these types of absorbent units.

BRIEF DESCRIPTION OF THE FIGURES

The disclosure will be described in greater detail below with reference to the figures shown in the appended drawings.

DETAILED DESCRIPTION

Different aspects of the present disclosure will be described more fully hereinafter with reference to the enclosed drawings. The disclosure can be realized in many different forms and should not be construed as being limited to the embodiments below.

Figure 1:
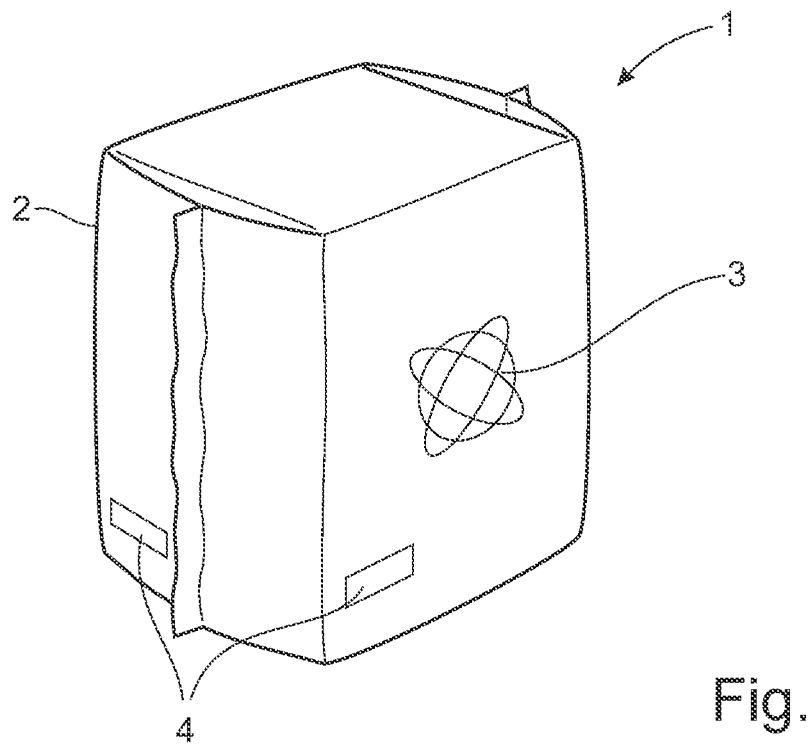
FIG. 1 shows a perspective view of a package of absorbent units according to a first embodiment.

With initial reference to FIG. 1, there is shown a perspective view of a package 1 which is intended to contain a number of absorbent units. The actual absorbent units are not visible in FIG. 1 but will be described in detail below with reference to FIGS. 2-4. It should be noted that the package 1 is suitable for absorbent units such as sanitary napkins, panty liners, diapers and incontinence pads, which can be packaged either with or without an individual wrapping. The package 1 is also suitable for other types of absorbent hygienic articles such as wet wipes.

The package 1 according to FIG. 1 is formed by an outer enclosure 2 which according to the embodiment is manufactured from a thin layer of a polymer material, suitably polyethylene, which is a flexible material which can be formed as a bag-like enclosure to accommodate the absorbent units. According to further embodiments, the outer enclosure 2 can be manufactured from other materials, for example polypropylene or cellulose-based materials, suitably in the form of a polyethylene film or film laminate, a LDPE (low density polyethylene film), a LDPE/LLDPE (linear low density polyethylene) film laminate, a LDPE/MDPE (medium density polyethylene) film laminate, or a LDPE/HDPE (high density polyethylene) film laminate.

In accordance with today's demands, the outer enclosure 2 is formed from a material which has a thickness which is not more than approximately 70 μm. According to an embodiment, the outer enclosure 2 has a thickness t of approximately 40-45 μm.

According to an embodiment, the outer enclosure 2 is provided with at least one graphical item 3, which according to the embodiment of FIG. 1 is in the form of a logotype which is printed on the outer enclosure 2. The outer enclosure 2 can also be provided with one or more additional graphical items 4. Also, as shown in FIG. 1, the graphical items 3, 4 can be applied on one or more of the side surfaces of the outer enclosure 2. Examples of graphical items which can be used are decorative drawings, photographs and text sections. These graphical items are normally printed on the outer enclosure 2. According to further embodiments, the graphical item can be in the form of one or more adhesive stickers which can be attached to the outer enclosure 2.

Figure 2:
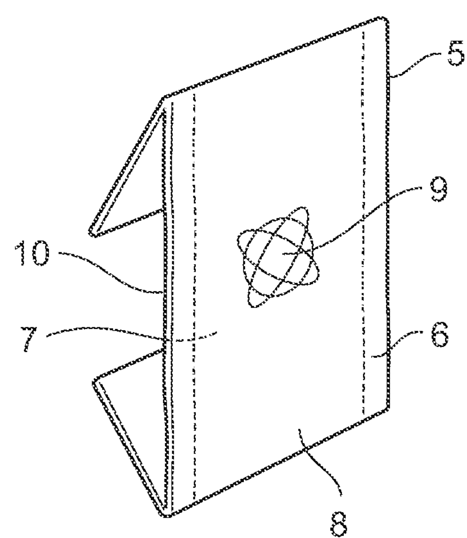
FIG. 2 shows a perspective view of an absorbent unit.
Figure 3:
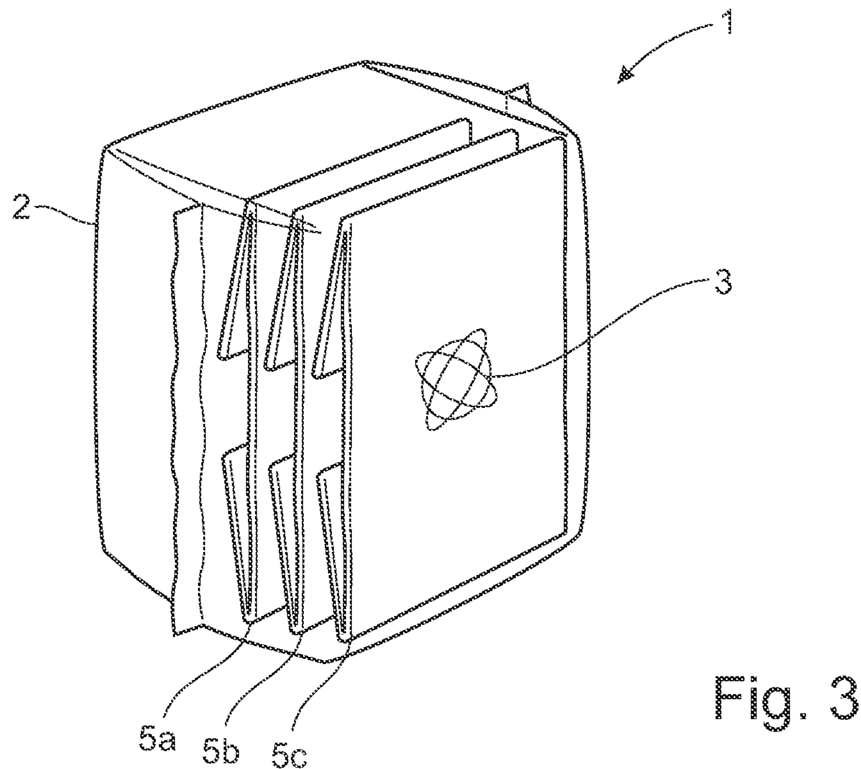
FIG. 3 shows a perspective view of a package showing also a number of absorbent units.

With reference to FIG. 2, there is shown an absorbent unit 5 which is intended to be packaged in the outer enclosure 2 of FIG. 1. The absorbent unit 5 is shown in a folded configuration. Also, during manufacturing of the package 1, a number of such absorbent units 5*a*, 5*b*, 5*c* are formed as a stack and are enclosed by the outer enclosure 2. This is shown in FIG. 3. For reasons of clarity, the outer enclosure 2 is drawn as a transparent component in FIG. 3. In reality, the absorbent units 5*a*, 5*b*, 5*c* are generally not intended to be visible from the outside.

According to an embodiment shown in FIG. 2, the absorbent unit 5 is constituted by an absorbent product in the form of a sanitary napkin which is designed and manufactured in a generally known manner. This means that it comprises a liquid-impermeable backsheet 6, a liquid-permeable topsheet 7 and an absorbent core 8 which is sandwiched between the backsheet 6 and the topsheet 7. The topsheet 7 is arranged at the surface of the absorbent unit 5 i.e. the side facing the wearer during use of the unit 5. The backsheet 6 is arranged at the underside of the absorbent unit 5, i.e. the side facing an undergarment (not shown) of the wearer during use.

As known, the absorbent unit 5 is configured as an absorbent structure for absorbing body exudates from a wearer in order to provide a dry, comfortable and odor-free feeling for the wearer. It should be noted that absorbent units 5 such as the one shown in FIG. 2 are generally known as such and for this reason they are not described in detail here.

According to the embodiment in FIG. 2, the absorbent product 5 comprises a further graphical item 9 in the form of a logotype, which can be designed with a similar visual appearance as the graphical item 3 on the surface of the outer enclosure 2. In a manner which corresponds to the outer enclosure 2, the graphical item 9 on the absorbent unit 5 can be in the form of a printed logotype, a drawing, a photograph or a text section, or alternatively an adhesive sticker. It should be noted that, in principle, the graphical item 9 on the absorbent unit 5 can be positioned on the backsheet 6, the topsheet 7 or even along a longitudinal edge 10 of the absorbent unit 5.

In the following, the graphical item 3 on the outer enclosure 2 will be referred to as a "first graphical item" 3 and the graphical item 9 on the absorbent unit 5 will be referred to as a "second graphical item" 9.

Also, the graphical items 3, 9 can be in the form of synchronized printed items, i.e. items which during manufacturing are positioned at a predetermined position on the outer enclosure 2 and the absorbent unit 5, respectively, or can alternatively be in the form of unsynchronized printed items.

The present disclosure is not limited to a package which necessarily must contain one or more graphical items such as logotypes, drawings, photographs, text sections or stickers which is applied on either the outer enclosure or the absorbent unit, or both. In fact, the principles behind the disclosure is equally applicable to packages which are formed without any such graphical items on the outer enclosure 2 or on the absorbent unit 5.

According to the embodiment shown in FIG. 2, the absorbent unit 5 is folded before being packaged in the outer enclosure 2. Also, with further reference to FIG. 3, a plurality of such absorbent units 5*a*, 5*b*, 5*c* will be stacked together in their folded condition so as to form the finished package 1. According to various embodiments, the absorbent units can be folded or unfolded, and can also be provided with one or more graphical items on various positions on any surface.

The disclosure relates to a package 1 of absorbent units 5 which comprises an outer enclosure 2 which is configured to enclose and accommodate the absorbent units 5. In this regard, it should be noted that today's design trends for absorbent products may require that the basic material of the outer enclosure 2 is chosen from materials having relatively light or pale colours, such as white, cream, light yellow, light pink, light blue, light green or other pastel-like colours. This means that the outer enclosure 2 may be based on a material which is at least partly non-opaque. As mentioned above, the outer enclosure 2 is according to an embodiment made of a thin flexible layer of polyethylene or a similar material. Furthermore, according to the embodiment shown in FIGS. 2 and 3, the outer enclosure 2 may support a first graphical item 3 and at least one of said absorbent units 5 (i.e. referred to as 5*a*, 5*b*, 5*c* in FIG. 3) may support a second graphical item 9.

For reasons explained above, it is an object of the disclosure to provide a package 1 which is configured so that generally no difference in colour can be perceived when comparing the colour of the outer enclosure 2 and the colour of the absorbent units 5, as regarded by a viewer from the outside of the package 1 and through the outer enclosure 2. In other words, the package 1 is configured so that there is generally no visible difference of the colours of the outer enclosure 2, on the one hand, and the absorbent units 5 as viewed through the outer enclosure 2, on the other hand. To this end, it is first noted that the outer enclosure 2 is at least partly of a first predetermined colour (L*1; a*1; b*1) as defined in the so-called L*a*b* colour space and the absorbent units 5 are at least partly of a second predetermined colour (L*2; a*2; b*2) in the L*a*b* colour space, as regarded through the outer enclosure 2. The absorbent units 5 can also be said to have a third predetermined colour (L*3; a*3; b*3) when regarded directly and not through the outer enclosure 2.

The so-called L*a*b* colour space, which is also referred to as CIELAB 1976, is a known colour space which is used for measuring colours of objects in different fields of technology. In the L*a*b* colour space, the term L* indicates the lightness of the object, whereas the terms a* and b* are chromaticity coordinates. As known to the skilled person, a chromaticity diagram for the L*a*b* colour space can be used so that +a* is the red direction, −a* is the green direction, +b* is the yellow direction and −b* is the blue direction. The centre of the diagram is achromatic, and as the a* and b* values increase, the saturation of the colour in question increase in a corresponding manner.

A numerical value of a colour can be denoted using the L*a*b* colour scale. Purely as an example, a certain first colour can be noted as L*1=47,19, a*1=+39,85, b*1=+18,14. A second colour can be noted, again only as an example, as L*2=49,21, a*2=+40,75, b*2=+16,01. Furthermore, the difference in colour between the two colours can then be expressed numerically by using the following terms: ΔL*=+2,02, Δa*=0,90, Δb*=−2,13.

Also, the difference in the colour space between the first and the second colour can be expressed as one single numerical value, ΔE, which indicates the magnitude of the colour difference. The value ΔE can be determined by using the following known equation:

$$\Delta E=\sqrt{(L*1-L*2)^2+(a*1-a*2)^2+(b*1-b*2)^2}$$

The present disclosure is based on the principle that the magnitude ΔE of the colour difference between the first colour corresponding to the outer enclosure 2 and the second colour corresponding to the absorbent units 5 is less than a predetermined limit value ΔEmax which is chosen so that generally no visible difference of the colours of the outer enclosure 2 and the absorbent units 5, as viewed from the outside of the package 1, can be perceived by a viewer.

According to an embodiment, the outer enclosure 2 is at least partly of a colour (L*1; a*1; b*1) which has a first colour value (a*1) which is within the interval from −22 to +26 and a second colour value (b*1) which is within the interval from −25 to +23. This corresponds to relatively light or pale colours for the outer enclosure 2, preferably pastel-like colours as mentioned above.

Figure 5:
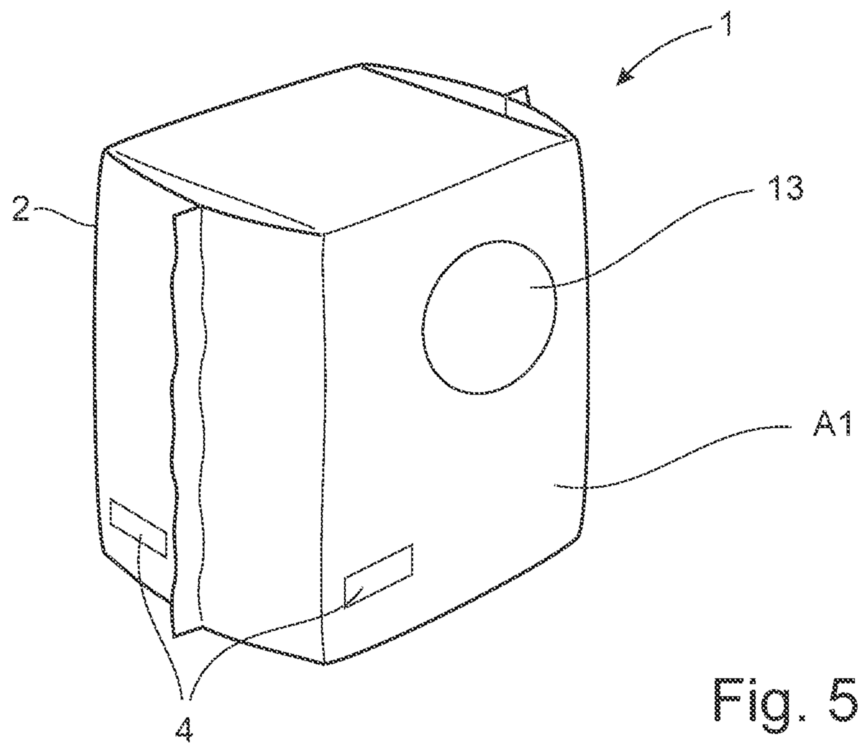
FIG. 5 shows a perspective view of a package according to a further embodiment.

Also, as mentioned above, the present disclosure is not limited to a package which necessarily must contain one or more graphical items on the outer enclosure or the absorbent unit. For this reason, and with reference to FIGS. 5 and 6, an embodiment will now be described in which the outer enclosure 2 has a particular area A1 with a lightness value L* which is at least 75. According to different embodiments, the lightness value L* for the area A1 is above 80, preferably above 85 and most preferably above 90.

This area A1 can be said to be a "dominant" area in the sense that it is perceived as corresponding to a substantial, or major, part of the outer enclosure 2 as regarded by a viewer. This is in accordance with today's trends relating to packages for absorbent products and contributes to the request to produce a package 1 which is coloured in very light and pale colours, i.e. colours having a relatively low amount of colouring substance.

According to an embodiment, the dominant area A1 constitutes at least 50% of the total area of the outer enclosure 2. According to further embodiments, the percentage is at least 60%, more preferably at least 70% and most preferably at least 80% of the total area of the outer enclosure 2.

Furthermore, the outer enclosure 2 also comprises a further part 13 having a colour or design which is different from that of the dominant area A1. The further part 13 can be a coloured section of the outer enclosure 2 and may also contain logotypes or other graphical items. The further part 13 can also be formed by differents geometries. Also, in the context of the present disclosure, the term "dominant area" also covers embodiments in which it can be considered to be composed of two or more partial areas which are delimited by the further part 13.

Figure 6:
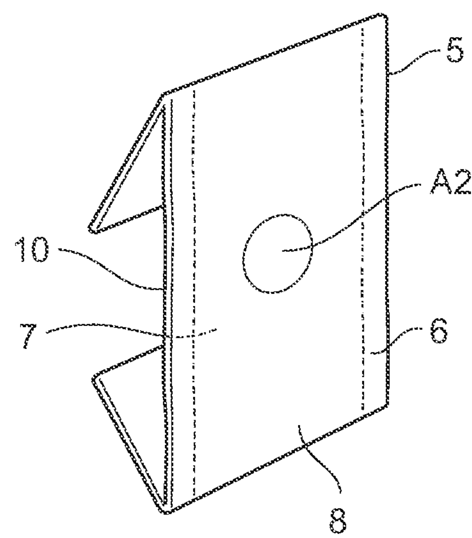
FIG. 6 shows a perspective view of an absorbent unit according to a further embodiment.

Furthermore, according to an embodiment and with reference to FIG. 6, the absorbent unit 5 has at least a further area A2 which is coloured, preferably lightly coloured, or alternatively light grey, i.e. not completely white. According to different embodiments, the lightness value L* of this further area A2 is at least 65 and preferably in the range of 80-93, more preferably in the range of 85-93 and most preferably in the range of 89-93.

According to the disclosure, the magnitude ΔE of the colour difference between the colour of the dominant area A1, i.e. (L*1; a*1; b*1) and the colour of the lightly coloured or light grey area A2 as seen through the outer enclosure 2, i.e. (L*2; a*2; b*2), is less than a predetermined limit value ΔEmax, which is chosen in a manner so that the absorbent units 5 are generally not visible through the outer enclosure 2. This means that generally no visible difference of the colour of the outer enclosure 2 and the colour of the absorbent units 5 as viewed through the outer enclosure 2 can be perceived by a viewer. In this manner, the above-mentioned object of configuring the package 1 so as to indicate to a customer that the absorbent product in question is of premium quality can be obtained.

Furthermore, according to an embodiment, the colours chosen for the outer enclosure 2 and the absorbent units 5 are selected in a manner so that the above-mentioned limit value ΔEmax is not more than 7, preferably not more than 6, more preferably not more than 5, even more preferably not more than 4 and most preferably not more than 3. This means that the colours which are chosen for the outer enclosure 2 and the absorbent units 5 are selected in a manner in relation to each other so that so that generally no visible difference of the colours of the outer enclosure 2 and the absorbent units 5 as regarded from outside the outer enclosure 2 is perceived by a viewer.

An example of a package using light and pastel-type colours may have a limit value ΔEmax which is approximately within the interval 2,3-5,6. However, as described above, this disclosure is not limited to such values only.

Furthermore, according to an embodiment, the outer enclosure 2 is manufactured from a material which has an opacity which is not higher than approximately 70%, preferably less than 60%, more preferably less than 50% and most preferably less than 40%. This corresponds to a material which is slightly transparent, which follows today's demands for packages having a modern and contemporary style.

Also, according to an embodiment, the outer enclosure 2 has a thickness t which is less than approximately 70 μm. According to further embodiments, the thickness t is preferably less than 60 μm, more preferably less than 50 μm, and most preferably within the interval 40-45 μm as mentioned above.

According to an embodiment as shown in FIGS. 1-3, the outer enclosure 2 is provided with a first graphical item 3 and the absorbent unit 5 is provided with a second graphical item 9. Also, the absorbent unit 5 which supports the second graphical item 9 is configured so that the second graphical item 9 is positioned in a manner in relation to said first graphical item 3 so that said second graphical item 9 is not visible through the outer enclosure 2. According to the embodiment shown in FIG. 3, this is accomplished by positioning the absorbent units 5*a*, 5*b*, 5*c* in a manner so that the second graphical item 9 is covered by the first graphical item 3 and for this reason is not visible from the outside of the package 1. In this regard, it should be noted that the second graphical item 9 as shown in FIG. 2 is positioned so that it faces the inside of the outer enclosure 2 whereas the first graphical item 3 is positioned on top of the second graphical item 9 so that it covers the second graphical item 9.

Figure 4:
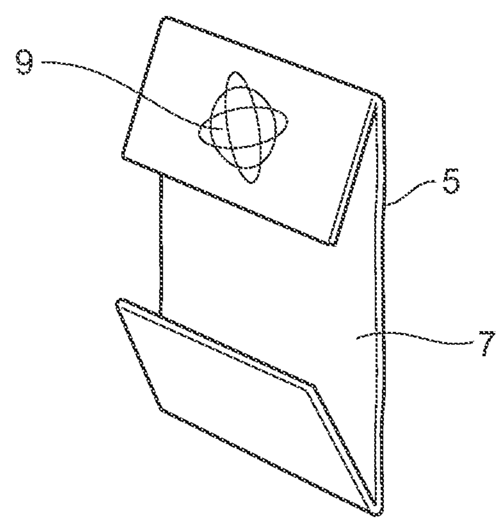
FIG. 4 shows a further perspective view of a further absorbent unit.

According to a further embodiment, which is shown in FIG. 4, the second graphical item 9 is placed on a side of the absorbent unit 5 which does not face the outer enclosure 2, i.e. so that the absorbent unit 5 is configured so that second graphical item 9 faces inwards into the interior of said outer enclosure 2. In this way also, the absorbent unit 5 will be configured so that the second graphical item 9 is positioned in a manner in relation to the first graphical item 3 so that said second graphical item 9 is not visible through the outer enclosure 2.

Furthermore, both the first graphical item 3 and the second graphical item 9 can, according to different embodiments, be constituted by printed logotypes, printed areas or areas comprising coloured sections, adhesive stickers or other graphical markings.

Figure 7:
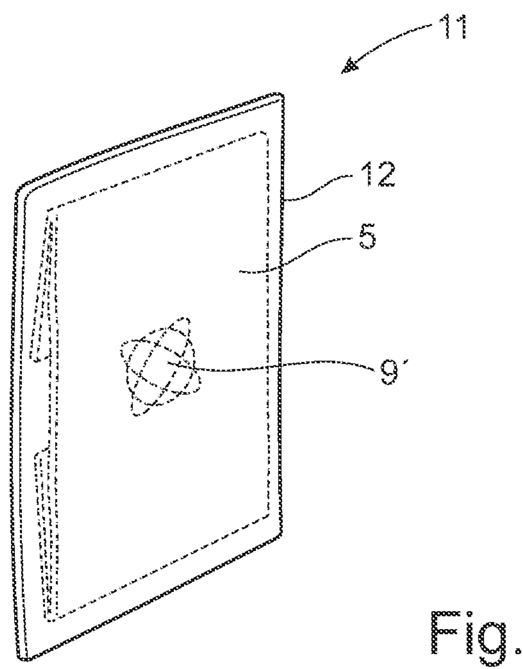
FIG. 7 shows a perspective view of an absorbent unit according to a further embodiment.

With reference to FIG. 7, there is shown a further embodiment involving an absorbent unit 11 which is constituted by an absorbent article 5 (of the same type as shown in FIG. 2) which is enclosed inside an inner enclosure 12. This inner enclosure 12 corresponds to an individual wrapping of the absorbent article 5, i.e. a wrapping sheet which encloses the absorbent article and which suitably is of the same type of material as the outer enclosure 2. Also, a second graphical item 9' is positioned on the outside of the inner enclosure 12. According to this embodiment, there is consequently no graphical item on the absorbent article 5 itself. Consequently, in the embodiment according to FIG. 5, the term "absorbent unit" is used to indicate a unit in the form of an absorbent article including an individual wrapping, which is another embodiment than an absorbent article without such individual wrapping (i.e. as shown in FIGS. 2 and 4). It should be noted that the disclosure is applicable to packages comprising either one of these types of absorbent units.

According to an embodiment, the outer enclosure 2 is manufactured from a material with an opacity which is not higher than a predetermined limit value. Suitably, this opacity limit value is approximately 70%. The opacity of a material corresponds to the degree to which light is not allowed to pass through it. Accordingly, a fully opaque material with 100% opacity is completely impervious to light, whereas a material with 0% opacity is completely transparent. Generally, increased opacity can be obtained by adding increasing amounts of titanium dioxide to the polymer melt from the material is manufactured, or by adding pigmented print.

Figure 8:
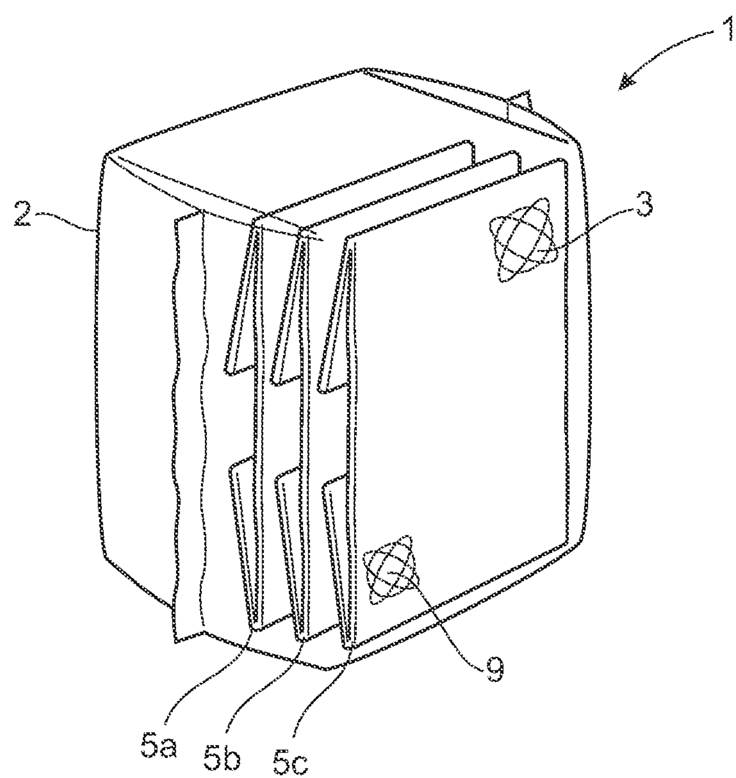
FIG. 8 shows a perspective view of an absorbent unit according to a further embodiment.

FIG. 8 shows an embodiment with an outer enclosure 2 which at least partly has an area with an opacity which is higher than said limit value, which is sufficient in order to prevent the second graphical item 9 from being visible from the outside. Consequently, the embodiment of FIG. 8 shows that the absorbent unit 5, which supports the second graphical item 9, is configured so that the second graphical item 9 is positioned in a manner so that it will not be visible for a viewer from outside the outer enclosure 2. More precisely, the second graphical item 9 is positioned so that it is aligned with at least the part of the outer enclosure 2 which has an area having an opacity which is higher than said limit value.

According to a further embodiment, the opacity value (0-100%) of the outer enclosure 2 can furthermore be chosen depending on the intensity of the second graphical item 9 so that the second graphical item 9 is not visible.

A process for manufacturing the package of absorbent units 2 as described above comprises a number of steps which will now be described. Initially, a material which is at least partially non-opaque is provided, in order to be used as an outer enclosure 2. The outer enclosure 2 has a thickness t which is not more than approximately 70 μm. Also, according to an embodiment, the opacity of the outer enclosure 2 is not higher than 70%.

Next, the outer enclosure 2 material is arranged so that it encloses a number of absorbent units 5; 11. Furthermore, according to embodiments described above and with reference for example to FIGS. 1 and 2, the outer enclosure 2 is configured so that it supports a first graphical item 3 of the type which is described above. Furthermore, the absorbent units 5; 11 are arranged so that they support a second graphical item 9; 9'. However, the outer enclosure 2 and the absorbent units 5 may alternatively lack graphical items.

Furthermore, the outer enclosure 2 is configured so that it has a first predetermined colour (L*1; a*1; b*1) as defined in the L*a*b* colour space, and the absorbent units 5 are configured with a second predetermined colour (L*2; a*2; b*2) in the L*a*b* colour space. Also, the absorbent units 5 are configured in a manner so that they have at least one lightly coloured or light grey area A2 and the outer enclosure has a dominant area A1 which covers a substantial part of the area of the outer enclosure 2 and has a lightness value L* which is above 75, in accordance with the description above.

Also, the outer enclosure 2 and the absorbent units 5; 11 are configured so that the magnitude ΔE of the colour difference between the dominant area A1 and the lightly coloured or light grey area A2 as seen through the outer enclosure 2 is less than a predetermined limit value ΔEmax which is chosen so that the absorbent units 5 are generally not visible through the outer enclosure 2.

According to a further embodiment, the absorbent unit 5; 11 which supports the second graphical item 9; 9' is configured so that the second graphical item 9; 9' is positioned so that the second graphical item 9; 9' is not visible for a viewer from outside of the outer enclosure 2.

In order to implement the embodiments of the present disclosure, the following description of measuring methods is provided.

Film Thickness:

The thickness of a film—such as the film being used for the outer enclosure 2—is measured with a foil thickness gauge, model 497 from Erichsen GmbH (or an equivalent apparatus). Thickness is measured under a pressure of 40 kPa. The pressure is applied from a circular foot with a diameter of about 6 mm.

Opacity:

Opacity is measured with a CM-5 spectrophotometer from Konica-Minolta (or an equivalent apparatus having diffuse illumination). Configure the spectrophotometer to the XYZ colour scale, D65 illuminant and 10° standard observer. Place the sample flat over the measurement aperture and cover the sample with the white ceramic standard plate that comes with the spectrophotometer. Take a first reading. Then cover the sample with a black standard plate and take a second reading. The opacity is then calculated as follows:

$$\text{Opacity }(\%)=(Y\text{ value with the black backing}/Y\text{ value with the white backing})\times 100$$

Representative measurements are taken all over the outer enclosure 2, and the mean opacity is reported.

Colour:

The principles for determining and defining colours and colour difference according to the L*a*b* colour space are described above.

Also, colour and colour difference is measured with CM-5 spectrophotometer from Konica-Minolta (or an equivalent apparatus). The apparatus illuminates the sample diffusely and detects the light at 8° from the normal line. Standard illuminant D65 and 10° standard observer are utilized. The instrument is set to SCE (specular component excluded). The tested area is placed flat and smooth against the spectrophotometer aperture (having a diameter of 30 mm). A white ceramic tile (coming with the spectrophotometer) having L* a* b* values at or very close to L*96.1, a* 0.1, b* 2.85 is placed behind all tested object, as a standard backing. For all measures described below, it is thus understood that this same standard white ceramic tile covers the outermost opposite surface of the tested object.

L* Value and Colour of the Absorbent Units 5:

An absorbent unit 5 is removed from the package 1. The unit is tested as found in the package, and it should not be unfolded or manipulated in any way. The operator selects a relevant area at will from the flat front or flat back side of the absorbent unit (the side edges are excluded). The area is placed over the 30 mm spectrophotometer aperture, and a reading is taken.

Magnitude of the Colour Difference ΔE Between the Outer Enclosure 2 and the Absorbent Units 5; 11 as Seen Through the Outer Enclosure 2:

The operator selects a 30 mm diameter area (a "significant area") on an unopened package, and measures L*, a* and b*. The operator then removes all absorbent units from the package, and measures L*a*b* on the same spot on the now isolated outer enclosure. The magnitude of the colour difference is then calculated according to the following formula:

$$\Delta E^*_{ab}=\sqrt{(L^*_2-L^*_1)^2+(a^*_2-a^*_1)^2+(b^*_2-b^*_1)^2}$$

Dominant Area, and L* Value of the Same:

Measurements relating to a dominant area, i.e. an area of a certain size having a lightness value L* which is higher than a predetermined limit value which according to an embodiment is 75, preferably higher than 80, more preferably higher than 85, and most preferably higher than 90 could be performed as follows. The absorbent units are removed from the package. The outer enclosure 2 is then cut along suitable lines, so that the outer enclosure 2 ends up essentially flat, but still in one piece. A maximum number of readings are then obtained on the outside (i.e. the side facing away from the absorbent units) of the flattened enclosure, without any measured 30 mm diameter area infringing upon another. The areas with L* values above a certain level are then compared to the total of the measured areas. For example, a piece of enclosure forms a square with dimensions 9×9 cm. A maximum of nine individual measurements fit into this area. If three samples obtain L* values below 75, and six samples obtain L* values above 75, then 67% of the outer enclosure is said to have an L* value above 75 in the context of this disclosure.

The invention is not limited to the embodiment but can be varied within the scope of the appended claims.

The invention claimed is:

1. A package of absorbent units, said package comprising:

an outer enclosure enclosing said absorbent units, the outer enclosure including a dominant area that is at least partially non-opaque, wherein said outer enclosure has a thickness which is less than approximately 70 μm, and wherein the dominant area of the outer enclosure is at least partly of a first predetermined colour as defined in the L*a*b* colour space, and the absorbent units are at least partly of a second predetermined colour in the L*a*b* colour space as viewed through the first predetermined colour of the dominant area of the outer enclosure;

wherein:

the absorbent units have at least one lightly coloured or light grey area, and the dominant area covers a substantial part of the outer enclosure and has a lightness value above 75 in the L*a*b* colour space, and a magnitude of a colour difference between the first colour of the dominant area and the lightly coloured or light grey area of the absorbent units, as seen through the first colour of the dominant area of the outer enclosure, is less than 7, wherein the magnitude of the colour difference is determined by the following equation:

$$\Delta E=\sqrt{(L^*1-L^*2)^2+(a^*1-a^*2)^2+(b^*1-b^*2)^2}.$$

2. A package according to claim 1, wherein the magnitude of the colour difference is less than 6.

3. A package according to claim 1, wherein the dominant area of the outer enclosure has an opacity which is not higher than approximately 70%.

4. A package according to claim 3, wherein the opacity of the dominant area of the outer enclosure is less than 60%.

5. A package according to claim 1, wherein the lightly coloured or light grey area has a lightness value which is at least 65.

6. A package according to claim 1, wherein the dominant area constitutes at least 50% of the total area of the outer enclosure.

7. A package according to claim 1, wherein the dominant area has a lightness value which is above 80.

8. A package according to claim 1, wherein said first predetermined colour has a first colour value which is within the interval from −22 to +26 and a second colour value which is within the interval from −25 to +23.

9. A package according to claim 1, wherein the thickness is less than approximately 60 μm.

10. A package according to claim 1, wherein the outer enclosure supports a first graphical item and at least one of said absorbent units supports a second graphical item, and wherein the absorbent unit is configured so that said second graphical item is positioned in a manner in relation to said first graphical item so that said second graphical item is not visible through the outer enclosure.

11. A package according to claim 10, wherein each one of said absorbent units is constituted by an inner enclosure which encloses an absorbent product, and wherein said second graphical item is positioned on an outside of said inner enclosure.

12. A package according to claim 10, wherein each one of said absorbent units is constituted by an absorbent product, and wherein said second graphical item is positioned on said absorbent product.

13. A package according to claim 10, wherein said second graphical item is positioned so that it faces an inside of the outer enclosure and wherein said first graphical item covers said second graphical item.

14. A package according to claim 10, wherein said first graphical item is arranged on an exterior side of said outer enclosure.

15. A package according to claim 10, wherein said first graphical item and said second graphical item are constituted by printed areas or areas comprising coloured sections, adhesive stickers, logotypes, text boxes or graphical markings.

16. A package according to claim 1, wherein said absorbent units are arranged in a folded configuration.

17. A package according to claim 1, wherein said outer enclosure has a thickness which is less than 50 μm.

18. A method for manufacturing a package of absorbent units, said method comprising:

providing an outer enclosure that includes a dominant area which is at least partially non-opaque and which outer enclosure has a thickness which is not more than approximately 70 μm;

arranging said outer enclosure so that it encloses said absorbent units;

providing the dominant area of the outer enclosure at least partly with a first predetermined colour as defined in the L*a*b* colour space; and providing the absorbent units at least partly with a second predetermined colour in the L*a*b* colour space as viewed through the first predetermined colour of the dominant area of the outer enclosure;

wherein said method comprises:

providing the absorbent units with at least one lightly coloured or light grey area;

providing a substantial part of the area of the outer enclosure with the dominant area which has a lightness value above 75 in the L*a*b* colour space; and configuring the package so that a magnitude of the colour difference between the first predetermined colour of the dominant area and the lightly coloured or light grey area as seen through the first predetermined colour of the outer enclosure is less than 7.

19. A method according to claim 18, wherein said outer enclosure has a thickness which is less than 50 μm.

* * * * *